United States Patent [19]

Schouteeten et al.

[11] Patent Number: 5,550,250
[45] Date of Patent: Aug. 27, 1996

[54] PREPARATION PROCESS FOR 2 FORMYL IMIDAZOLE ACETALS

[75] Inventors: Alain Schouteeten, Ezanville; Yani Christidis, Paris, both of France

[73] Assignee: Societe Francaise Hoechst, Puteaux, France

[21] Appl. No.: 511,251

[22] Filed: Aug. 4, 1995

[51] Int. Cl.$^6$ .................... C07D 405/04; C07D 233/64
[52] U.S. Cl. ............................. 548/311.1; 548/341.1
[58] Field of Search ........................ 548/341.1, 311.1

[56] References Cited

U.S. PATENT DOCUMENTS

| | | | |
|---|---|---|---|
| 3,652,579 | 3/1972 | Hoffer et al. | 260/309 |
| 5,312,927 | 5/1994 | Takada et al. | 548/335.1 |

FOREIGN PATENT DOCUMENTS

| | | |
|---|---|---|
| 0249530A3 | 12/1987 | European Pat. Off. |
| 0316672A1 | 5/1989 | European Pat. Off. |
| 58-89294 | 5/1983 | Japan . |

OTHER PUBLICATIONS

Koople et al, Quaternary Salts of 2–[(Hydroxyimino)methyl]imidazole . . . J. Med. Chem, No. 4, vol. 34, pp. 1368–1376, 1991.

J. Adamson et al, Cyclic Quaternary Ammonium Salts J. Chem. Soc., vol. 16, pp. 2748–2749, 1971.

I. Antonine et al, The Decarbonylation Reaction of Imidazole–2–carbaldehydes in Ethanol, Journal of Heterocyclic Chemistry, No. 7, vol. 15, pp. 1201–1203, 1978.

Hagedorn III, et al, "Cardiotonic Agents. etc" J. Med. Chem. (1987), 30, 1342–1347.

Lukowski, "2–Methylinedazole", CA86:89825u (1977).

*Primary Examiner*—Patricia L. Morris
*Attorney, Agent, or Firm*—Browdy and Neimark

[57] ABSTRACT

Preparation process for a product of formula (I):

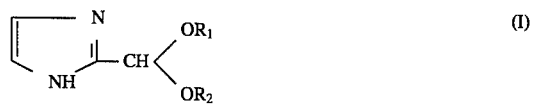

in which $R_1$ and $R_2$, either are identical and represent a $C_1$–$C_4$ alkyl radical, or form together a group of formula (II):

$$-CHR_3-(CR_4R_5)_n-CHR_6- \quad (II)$$

in which $R_3$, $R_4$, $R_5$ and $R_6$, identical or different, represent a hydrogen atom or a $C_1$–$C_4$ alkyl radical, and n represents 0 or 1, in which an aqueous mixture of glyoxal and an ethanal of formula (III):

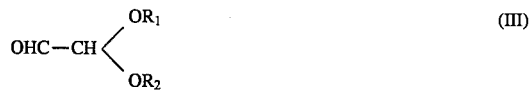

in which $R_1$ and $R_2$ have the meaning given above, is reacted with ammonia.

4 Claims, No Drawings

PREPARATION PROCESS FOR 2 FORMYL IMIDAZOLE ACETALS

FIELD OF THE INVENTION

The present invention relates to a process for preparing 2-formyl imidazole acetals.

BACKGROUND OF THE INVENTION 2-formyl imidazole is a widely-described product, some of the acetals of which are known, such as, in particular 2-dimethoxymethyl imidazole (Gary A. KOOLPE et al., J. Med. Chem., 1991, 34, 1368–1376; T. S. MANOHARAN et al., J. Org. Chem., 1988 53, 1107–1110), which compounds are obtained by standard acetalization of the aldehyde group. As for 2-formyl imidazole, it can be obtained either by oxidation of 2-hydroxymethyl imidazole, or by formylation of imidazole whose NH function is transitorily substituted by a protector group, or finally by hydrolysis of one of its aminal derivatives U.S. Pat. No. 3,812,189; K. L. KIRK, J. Org. Chem., 1978, 43, 4381–4383; L. A. M. BASTIAANSEN et al., J. Org. Chem., 1986, 51, 1891–1894). 2-formyl imidazole and its acetals are raw materials useful for obtaining various products which have valuable therapeutic or plant-protective properties. It is therefore beneficial to be able to have available a process which allows 2-formyl imidazole or one of its acetals to be obtained rapidly and economically in a single stage starting from inexpensive raw materials. With this aim in mind, the Applicant was surprised to discover a simple and rapid process allowing the preparation, in a single stage, of 2-formyl imidazole acetals.

SUMMARY OF THE INVENTION

Therefore a subject of the present invention is a process for preparing a product of formula (I):

in which $R_1$ and $R_2$, either are identical and represent a $C_1$–$C_4$ alkyl radical, or together form a group of formula (II):

in which $R_3$, $R_4$, $R_5$ and $R_6$, identical or different, represent a hydrogen atom or a $C_1$–$C_4$ alkyl radical, and n represents 0 or 1, characterized in that an aqueous mixture of glyoxal and an ethanal of formula (III):

in which $R_1$ and $R_2$ have the meaning given above, is reacted with ammonia.

The expression $C_1$–$C_4$ alkyl radical can designate, for example, a methyl, ethyl, n-propyl, methyl ethyl, n-butyl, 1-methyl or 2-methyl propyl radical.

The products of formula (III) are products which can be prepared by one of the methods described in the European Patent Application No. 249530 or 316672, and some of them are commercial products.

In the preferred conditions for implementing the invention, the process described above is carried out:

in an aqueous medium,
at a temperature of less than 60° C.,
with an excess of ammonia and/or of glyoxal.

DETAILED DESCRIPTION OF THE INVENTION

The following examples illustrate the invention without however limiting it.

EXAMPLE 1

805 g of an aqueous solution containing 153.3 g (9 moles) of ammonia is heated to 40° C., under agitation, then 955 g of an aqueous solution containing 209 g (3.6 moles) of glyoxal and 312.3 g (3 moles) of 2,2-dimethoxy ethanal is introduced over one hour into this agitated solution, maintained at 45°–50° C. by gentle external cooling. Once the introduction is complete, the solution obtained is heated for 4 hours at 60° C., then it is concentrated under reduced pressure at 60° C. to about 900 g and it is finally cooled down to about 15° C. The expected product crystallizes spontaneously; it is isolated by filtration then recrystallized hot and cold from about 500 g of water. In this way 291.3 g ( 2.05 moles ) of 2-dimethoxymethyl imidazole crystallized as colourless prisms is obtained, having a melting point of 122° C. (literature cited M.p.=120°–121° C.), $^1$H NMR (CDCl$_3$) δ 3.37 (s, 6H, 2CH$_3$), 5.50 (s, 1H, CH), 7.06 (s, 2H, aryl), 10.0 (s, 1H, NH).

EXAMPLE 2

Example 1 is reproduced using only 3 moles of glyoxal instead of 3.6 moles. In this way 251.6 g (1.77 moles) of 2-dimethoxymethyl imidazole is obtained having a melting point of 122° C.

We claim:

1. A process for preparing a product of formula (I):

in which $R_1$ and $R_2$, either are identical and represent a $C_1$–$C_4$ alkyl radical, or together form a group of formula (II):

in which $R_3$, $R_4$, $R_5$ and $R_6$, identical or different, represent a hydrogen atom or a $C_1$–$C_4$ alkyl radical, and n represents 0 or 1, comprising reacting an aqueous mixture of glyoxal and an ethanal of formula (III):

in which $R_1$ and $R_2$ have the meaning given above, is reacted with ammonia.

2. A process according to claim 1 wherein the reaction is conducted at a temperature of less than 60° C.

3. A process according to claim 1 wherein $R_1$ and $R_2$ together form a group of formula (II):

4. A process according to claim 1 wherein $R_1$ and $R_2$ are the same or different and are selected from the group consisting of $C_1$–$C_4$ alkyl radicals.

* * * * *